United States Patent
Ali et al.

(10) Patent No.: US 12,161,660 B1
(45) Date of Patent: *Dec. 10, 2024

(54) NANO-SIZED CHITOSAN/VS$_2$ NANOCOMPOSITE LIKE FLOWERS FOR POTENTIAL PHARMACEUTICAL APPLICATIONS

(71) Applicant: KING FAISAL UNIVERSITY, Al-Ahsa (SA)

(72) Inventors: Mai Mostafa Khalaf Ali, Al-Ahsa (SA); Hany Mohamed Abd El-Lateef Ahmed, Al-Ahsa (SA); Enas T. Aljohani, Majmaah (SA); Hessah A. Al-Abdulkarim, Riyadh (SA); Ahmed M. Abu-Dief, Sohag (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/507,324

(22) Filed: Nov. 13, 2023

(51) Int. Cl.
*A61K 39/395* (2006.01)
*A61K 31/722* (2006.01)
*A61K 47/02* (2006.01)
*A61P 31/04* (2006.01)
*A61P 35/00* (2006.01)

(52) U.S. Cl.
CPC ............ *A61K 31/722* (2013.01); *A61K 47/02* (2013.01); *A61P 31/04* (2018.01); *A61P 35/00* (2018.01); *A61K 2121/00* (2013.01)

(58) Field of Classification Search
None
See application file for complete search history.

(56) References Cited

U.S. PATENT DOCUMENTS

2021/0289791 A1   9/2021   Green et al.

FOREIGN PATENT DOCUMENTS

CN   111773429 A   10/2020
KR   101562860 B1   10/2015

OTHER PUBLICATIONS

Lakkakula et al, Materials Science Engineering C70 p. 169-177, 2017.*
Xu et al, International Journal of Biological Macromolecules, vol. 220, p. 124-134, 2022.*
Yang et al., Sensors and Actuator, vol. 346, p. 1-7 (Year: 2021).*
Kasinathan, et al.; "Fabrication of eco-friendly chitosan functionalized few-layered WS2 nanocomposite implanted with ruthenium nanoparticles for in vitro antibacterial and anticancer activity: Synthesis, characterization, and pharmaceutical applications." https://doi.org/10.1016/j.ijbiomac.2021.08.153.
Fakhri, et al.; (2018). "Preparation and characterization of WS2 decorated and immobilized on chitosan and polycaprolactone as biodegradable polymers nanofibers: Photocatalysis study and antibiotic-conjugated for antibacterial evaluation." International Journal of Biological Macromolecules, 120(), 1789-1793. doi:10.1016/j.ijbiomac. 2018.09.207.
Kasinathan, et al.; "Facile Synthesis of 2d Chitosan Based Nanocomposite for in Vitro Biomedical and Photocatalytic Applications." http://dx.doi.org/10.2139/ssrn.4211155.
Zare, et al.; (2021). "Nonspherical Metal-Based Nanoarchitectures: Synthesis and Impact of Size, Shape, and Composition on Their Biological Activity." Small, 17(17), 2007073. doi: 10.1002/smll. 202007073.
Rajoka, et al.; (2019). "Chitosan and its derivatives: synthesis, biotechnological applications, and future challenges." Applied Microbiology and Biotechnology, (), -. Doi: 10.1007/s00253-018-9550.
Dinh, et al.; (2020). "Chitosan-MnO2 nanocomposite for effective removal of Cr (VI) from aqueous solution." Chemosphere,257,127147. doi:10.1016/j.chemosphere.2020.127147.
Huang, et al.; (2014). "Molybdenum disulfide nanoflower-chitosan-Au nanoparticles composites based electrochemical sensing platform for bisphenol A determination." Journal of Hazardous Materials, 276, 207-215. doi:10.1016/j.jhazmat.2014.05.037.

* cited by examiner

*Primary Examiner* — Yunsoo Kim
(74) *Attorney, Agent, or Firm* — Nath, Goldberg & Meyer; Joshua B. Goldberg

(57) ABSTRACT

A nano-sized chitosan/VS$_2$ nanocomposite for use in various pharmaceutical applications. The nano-sized chitosan/VS$_2$ nanocomposite can be formed as a flower nanocomposite.

2 Claims, 1 Drawing Sheet

NANO-SIZED CHITOSAN/VS$_2$ NANOCOMPOSITE LIKE FLOWERS FOR POTENTIAL PHARMACEUTICAL APPLICATIONS

BACKGROUND

1. Field

The present disclosure relates to a nano-sized chitosan/VS$_2$ nanocomposite for use in various pharmaceutical applications.

2. Description of the Related Art

Recently, nanotechnology has begun to be investigated for use in obtaining nanoscale materials with antibacterial properties in order to create novel therapeutic goods and efficient prophylactic and treatment methods for infections. Naturally occurring polysaccharides have been utilized as powerful templates for stabilizing a variety of metal ions, metal sulfides, and metal oxides because of their low toxicity, low cost, and excellent biological properties. For this purpose, numerous polymer-supported metal or metal oxide nanocomposite materials have been designed in an attempt to find materials providing unique properties and fit many applications not achievable separately by each component. Currently, a growing interest among researchers is the design and growth of metal oxide polymer complexes that can be successfully utilized in many applications like water treatment, nano catalysis, and as biologically active agents, among many other applications.

Chitosan (CS), the partial deacetylated form of chitin, is prepared via alkaline deacetylation under certain conditions. During this process, acetamide groups are converted into primary amino groups, as shown below. Chitosan has been intensively utilized due to its superior biodegradability, biocompatibility, low toxicity, and film forming properties. Chitosan and its derivatives have a wide range of biological activities that have been widely explored, particularly in biomedical science. Chitosan and its derivatives, more so than most other polysaccharides, are considered as powerful templates for the preparation of metal oxide nanoparticles owing to their unique ability to combine with metal ions via the hydroxyl and amino groups.

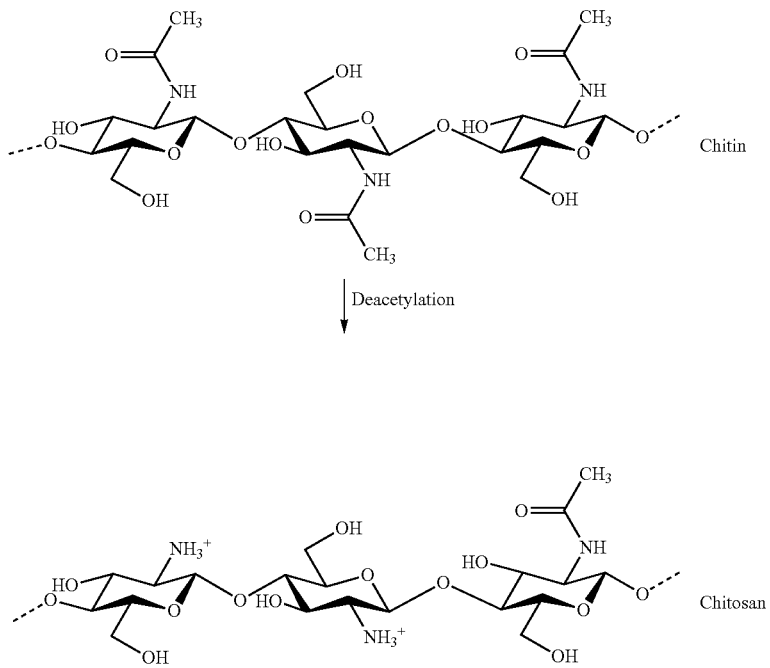

FIG. 1. Structures of chitosan and chitin.

So far, numerous effective techniques such as chemical vapor deposition, electro-Fenton processing, electrodeposition, liquid exfoliation, solvothermal methods, and microwave heating processes, have been carried out to synthesize transition metal dichalcogenide (TMDC) materials like VS$_2$. These techniques frequently have drawbacks because they take an extended period of time, require difficult conditions, and/or utilize risky and expensive organic solvents.

Accordingly, compositions and methods solving the aforementioned problems are desired.

SUMMARY

The present subject matter relates to the use of a combination of hydrothermal and calcination synthesis methods as the most advantageous for the economy and the environment. Such methods result in a novel chitosan/VS$_2$ nanocomposite which has never previously been achieved and having various pharmaceutical applications.

Accordingly, the present subject matter relates to a chitosan/VS$_2$ nano composite having the formula:

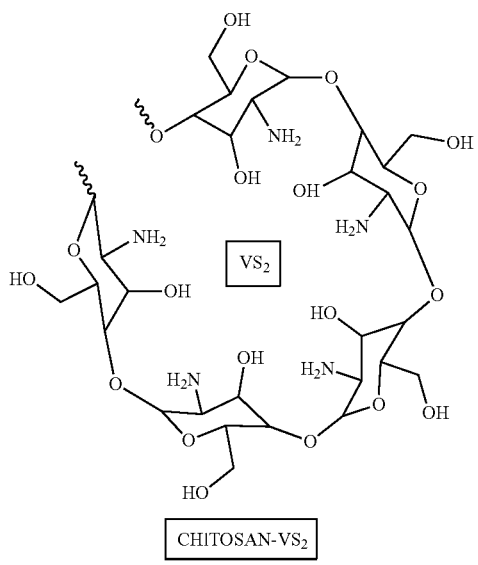

In one embodiment, the present subject matter relates to a method for making the chitosan/VS$_2$ nano composite described herein, the method comprising: stirring chitosan in an acetic acid solution to produce a chitosan solution; adjusting pH of the chitosan solution to a pH of about 6 to about 7 to obtain a pH adjusted chitosan solution; adding a VS$_2$ nanoflower to the pH adjusted chitosan solution while stirring to obtain a mixture; drying the mixture to remove any remaining acetic acid; and obtaining the chitosan/VS$_2$ nano composite.

In an embodiment, the present subject matter relates to a method for treating a microbial infection in a patient, the method comprising administering a microbial treating effective amount of the chitosan/VS$_2$ nano composite as described herein to a patient in need thereof.

In another embodiment, the present subject matter relates to a method for treating cancer in a patient, the method comprising administering a cancer treating effective amount of the chitosan/VS$_2$ nano composite as described herein to a patient in need thereof.

In a further embodiment, the present subject matter relates to a method for promoting an antioxidant effect in a patient, the method comprising administering an antioxidant amount of the chitosan/VS$_2$ nano composite as described herein to a patient in need thereof.

These and other features of the present subject matter will become readily apparent upon further review of the following specification.

DETAILED DESCRIPTION OF THE PREFERRED EMBODIMENTS

Figure 1A:
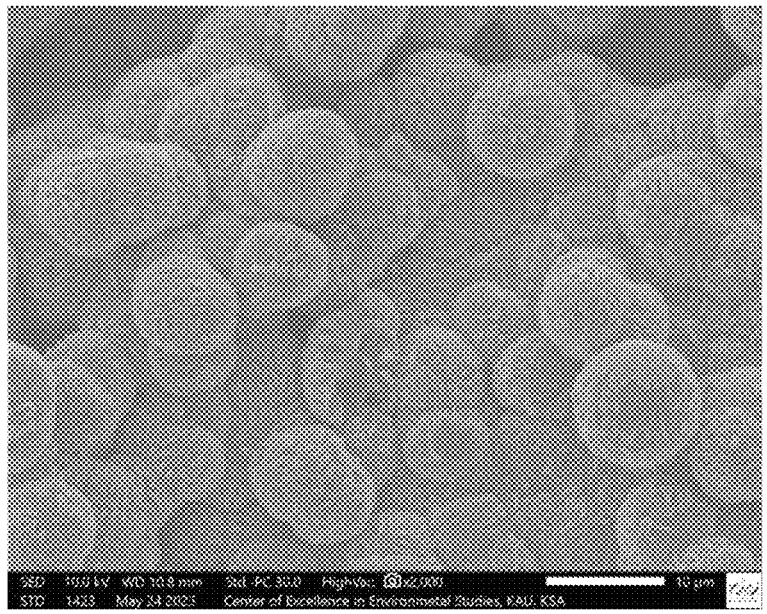
FIGS. 1A-1B show FESEM images of pure VS$_2$ (FIG. 1A) and the present chitosan/VS$_2$ nanocomposite (FIG. 1B).
Figure 1B:
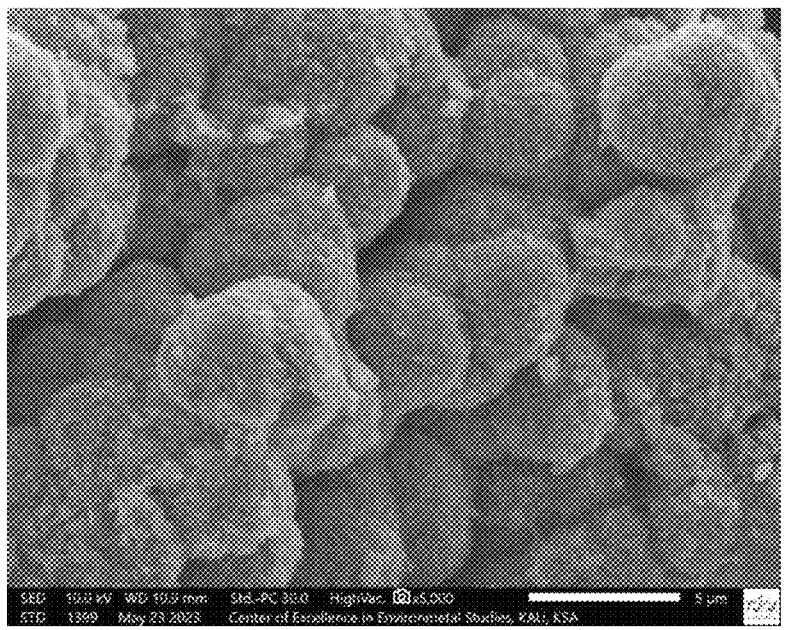

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as by way of non-limiting example a microbial infection, cancer, or an antioxidant needing condition.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the use of a combination of hydrothermal and calcination synthesis methods as the most advantageous for the economy and the environment. Such methods result in a novel chitosan/VS$_2$ nanocomposite which has never previously been achieved and having various pharmaceutical applications.

Accordingly, the present subject matter relates to a chitosan/VS$_2$ nano composite having the formula:

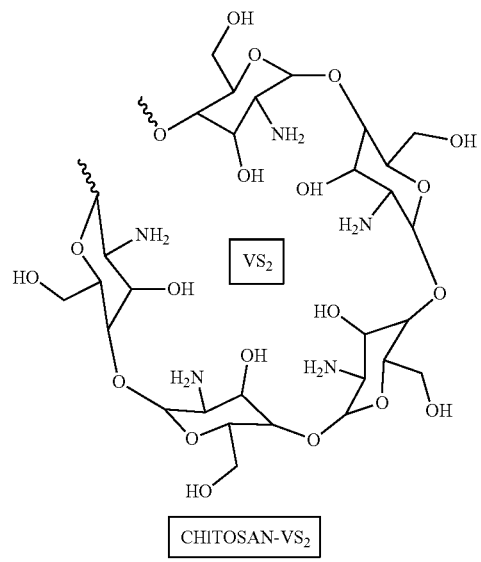

CHITOSAN-VS$_2$

In certain embodiments, the chitosan/VS$_2$ nano composite can be formed as flower-like particles.

In additional embodiments, the VS$_2$ can be immobilized on the chitosan.

In further embodiments, the chitosan/VS$_2$ nano composite can have antibacterial, antifungal, and anti-cancer properties.

In one embodiment, the present subject matter relates to a method for making the chitosan/VS$_2$ nano composite described herein, the method comprising: stirring chitosan in an acetic acid solution to produce a chitosan solution; adjusting pH of the chitosan solution to a pH of about 6 to about 7 to obtain a pH adjusted chitosan solution; adding a VS$_2$ nanoflower to the pH adjusted chitosan solution while stirring to obtain a mixture; drying the mixture to remove any remaining acetic acid; and obtaining the chitosan/VS$_2$ nano composite.

In an embodiment of the present production methods for making the chitosan/VS$_2$ nano composite, the chitosan can be stirred in the acetic acid solution for about 5 hours.

In another embodiment of the present production methods for making the chitosan/VS$_2$ nano composite, the chitosan solution can have a concentration of chitosan of about 2% w/v.

In a further embodiment of the present production methods for making the chitosan/VS$_2$ nano composite, the pH of the chitosan solution can be adjusted by adding a 0.5 M NaOH solution.

In an additional embodiment of the present production methods for making the chitosan/VS$_2$ nano composite, the mixture can be dried for about 4 hours at about 60° C.

In one embodiment of the present production methods for making the chitosan/VS$_2$ nano composite, the dried mixture can be dehydrated.

In an embodiment, the present subject matter relates to a method for treating a microbial infection in a patient, the method comprising administering a microbial treating effective amount of the chitosan/VS$_2$ nano composite as described herein to a patient in need thereof.

In one embodiment, the microbial infection is caused by bacteria. In one embodiment in this regard, the microbial infection can be caused by *Pseudomonas* bacteria. In another embodiment in this regard, the microbial infection can be caused by a fungus.

In another embodiment, the present subject matter relates to a method for treating cancer in a patient, the method comprising administering a cancer treating effective amount of the chitosan/$VS_2$ nano composite as described herein to a patient in need thereof. In an embodiment in this regard, the cancer can be colon cancer.

In a further embodiment, the present subject matter relates to a method for promoting an antioxidant effect in a patient, the method comprising administering an antioxidant amount of the chitosan/$VS_2$ nano composite as described herein to a patient in need thereof.

The present teachings are illustrated by the following examples.

EXAMPLES

Example 1

Preparation of the Chitosan-$VS_2$ Flower Like Nanocomposite

A calculated amount of chitosan (1 g) was swirled for 5 h at room temperature with a magnetic agitator in a 1% (v/v) acetic-acid solution to produce a chitosan solution of 2% (w/v). The pH of the resultant chitosan solution was brought up to the pH range of 6-7 by gradually adding a calculated amount of 0.5 M NaOH solution while continuously stirring. The anticipated quantity of $VS_2$ 4%) nano-flower was then gradually added to the Chitosan solution, portion by portion, while the mixture was continuously stirred. The chitosan-$VS_2$ nanocomposite was obtained by firstly cast of the above solution into a 100 mm Petri dish, drying there for 4 hrs at 60° C. to get rid of any remaining acetic acid, and then removed. The chitosan-$VS_2$ nanocomposite was dehydrated at 60° C. and rinsed with distilled water before fully dried and further used for characterization.

Example 2

Antimicrobial Activity

To evaluate antimicrobial activity, the bacterial strain (*Pseudomonas* (-ve)), and fungal (*Aspergillus flavus*), were used. These strains cultured in nutrient agar and Muller-Hinton medium. Ofloxacin and Fluconazole compounds were used as standard drug for comparison.

The susceptibilities of such growth rate of microorganisms were measured in vitro by agar well diffusion method. The tested nano complex was dissolved in dimethylsulfoxide at different concentrations (10 and 20 mg/ml). 1 $cm^3$ of a 24 h broth culture containing $10^6$ $CFU/cm^3$ was placed in sterile Petri-dishes. Molten nutrient agar (15 $cm^3$) maintained at 45° C. was then poured into the Petri-dishes and allowed to solidify. Then holes of 6 mm diameter were formed in the agar using a sterile cork borer and these holes were completely filled with the test solutions. The plates were incubated for 24 h at 37° C. After the incubation period, the zone of inhibition of each well was determined by measuring the zones of growth inhibition (mm) against the test microorganisms with zone reader (Hi Antibiotic zone scale). In order to clarify the effect of solvent (DMSO) on the biological screening, DMSO alone was used as control, and it showed no activity against microbial strains. The measurements were made in triplicate for each compound and their average values are reported.

Antifungal activities of the prepare nano-complex were studied against three fungal cultures using the well diffusion method. The tested fungi were inoculated in Sabouraud dextrose broth medium (Hi-Media Mumbai) and incubated at 35° C. for 72 h and subsequently a suspension of about $1.60 \times 10^4$-$6.00 \times 10^4$ c.f.u/ml was introduced agar plates and a sterile glass spreader was used for even distribution of the inoculum. The discs measuring 6 mm in diameter were prepared from Whatman No. 1 filter paper and sterilized by dry heat at 140° C. for 1 h. The sterile discs previously soaked in known concentration of the tested compounds were placed in Sabouraud dextrose Agar (SDA) plates. The plates were inverted and incubated at 35° C. for 7 days. The susceptibility was assessed on the basis of diameter of inhibition against *albicans* and non-*albicans* strain of fungi.

Minimum inhibitory concentrations (MICs) are defined as the lowest concentration of an antimicrobial that will inhibit the visible growth of a microorganism after overnight incubation. MICs are used by diagnostic laboratories mainly to confirm resistance of microorganism to antimicrobial agents and also to monitor the activity of new antimicrobial agents. MIC was determined in vitro in liquid medium by serial broth dilution method. The MIC values keep up a correspondence to the most minuscule concentrations that did not allow for the recognition of any visible growth.

Example 3

Anticancer Activity

The anticancer activity was made at the National Cancer Institute, Cancer Biology Department, Pharmacology Department, Cairo University. The absorbance or optical density (O.D.) of each well was measured spectrophotometrically at 564 (nm) with an "ELIZA" micro plate reader (Meter tech. Σ 960, "USA"). Evaluation of the cytotoxic activity of the prepared nano-complex was carried out against Breast cancer cells line. The evaluation process was carried out in vitro using the Sulfo-Rhodamine-B-stain (SRB). Cells were placed in 96-multiwell plate ($10^4$ cells/well) for 24 hrs before processing with the complexes to allow attachment of cell to the wall of the plate. Various concentrations of the compounds under test in DMSO (0, 1, 2.5, 5 and 10 µM) were added to the cell monolayer. Monolayer cells were incubated with the complexes for 48 hrs at 37° C. and in atmosphere of 5% $CO_2$. After 48 hrs, cells were fixed, rinsed, and stained with Sulfo-Rhodamine-B-stain. Excess stain was washed with acetic acid and attached stain was treated with Tris EDTA buffer. Color intensity was measured in an ELISA reader. $IC_{50}$ was evaluated and potency was calculated with regard to percentage of change of (vistabline standard). The relation between surviving fraction and compound concentration is plotted to get the survival curve of each tumor cell line after the specified compound. The experiment was carried out once and each concentration repeated 3 times.

The inhibitory concentration percent (IC %) was estimated according to the equation for Inhibition concentration:

$$(IC) \% = (\text{Control O.D.} - \text{Ligand O.D.}) \times 100 / \text{Control O.D}$$

The prepared chitosan-$VS_2$ like flower nanocomposite show super anticancer activity with $IC_{50}$ 1.25 µg/µl against a colon cancer cell line compared with the vinblastine standard drug ($IC_{50}$=4.75 µg/µl)

Example 4

Antioxidant Activity

In vitro antioxidant activity of the newly nano-complex was evaluated using scavenging the stable DPPH radical modified method. The model of scavenging the stable DPPH radical is a method that is widely used to evaluate antioxidant activities in a relatively short time compared with other methods. DPPH' radical scavenging test relies on the absorbance change of the radical when deactivated by antioxidants, which easily observable with naked eye as color changes from purple to yellow. Stock solutions of the investigated compounds were dissolved in methanol-DMSO (4:1) was diluted to final concentration of 10, 25, 50, 100 and 150 M. Methanolic DPPH (2,2-diphenyl-1-picrylhydrazyl) solution (1 mL, 0.3 mmol) was added to 3.0 mL of the synthesized compounds as well as standard compound (Ascorbic acid). The tube was protected from light by covering with aluminum foil and the absorbance was measured at 517 nm after 30 min. using methanol as a blank. All the tests were made in triplicates. Vitamin C was used as standard or positive control, parallel to the test compound and in the absence of the test compound/standard used as the negative control. The reduction in the absorbance of DPPH was calculated relative to the measured absorbance of the control. Lower absorbance values of reaction mixture indicated higher free-radical-scavenging activity.

The percentage of DPPH radical scavenging activity was calculated using the below equation:

$$\% DPPH \text{ scavenging activity} = \frac{A_C - A_S}{A_C}$$

where $A_C$ is the absorbance of the L-ascorbic acid (Standard) and $A_S$ is the absorbance of different compounds. The methanolic DPPH solution (1 mL, 0.3 mM) was used as control. The effective concentration of sample required to scavenge DPPH radical by 50% (IC50 value) was obtained by linear regression analysis of dose-response curve plotting between % inhibition and concentrations.

The prepared chitosan-$VS_2$ like flower nanocomposite shows super Anti-oxidant activity with $IC_{50}$ of 5.5 µg/µl compared with l-ascorbic acid standard antioxidant (IC50=50.8 µg/µl).

It is to be understood that the chitosan $VS_2$ nano composite is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A chitosan/VS2 nano composite having the formula:

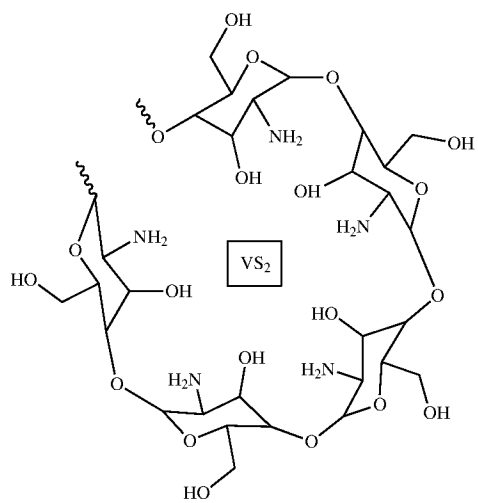

wherein the chitosan/$VS_2$ nano composite is formed as flower-like particles, and the $VS_2$ is immobilized on the chitosan.

2. The chitosan/$VS_2$ nano composite of claim 1, wherein the chitosan/$VS_2$ nano composite has antibacterial, antifungal, and anti-cancer properties.

* * * * *